(12) United States Patent
Rantala

(10) Patent No.: US 8,565,863 B2
(45) Date of Patent: Oct. 22, 2013

(54) ECG FRONT END AND METHOD FOR ACQUIRING ECG SIGNALS

(75) Inventor: Börje Rantala, Helsinki (FI)

(73) Assignee: General Electric Company, Schenectady, NY (US)

(*) Notice: Subject to any disclaimer, the term of this patent is extended or adjusted under 35 U.S.C. 154(b) by 585 days.

(21) Appl. No.: 12/817,540

(22) Filed: Jun. 17, 2010

(65) Prior Publication Data

US 2011/0313305 A1  Dec. 22, 2011

(51) Int. Cl.
*A61B 5/0432* (2006.01)

(52) U.S. Cl.
USPC .......................................... 600/509

(58) Field of Classification Search
USPC ................... 600/509, 513, 515, 518
See application file for complete search history.

(56) References Cited

U.S. PATENT DOCUMENTS

2005/0251003 A1* 11/2005 Istvan et al. ............. 600/393

* cited by examiner

*Primary Examiner* — Kennedy Schaetzle
*Assistant Examiner* — Erica Lee
(74) *Attorney, Agent, or Firm* — Andrus, Sceales, Starke & Sawall, LLP

(57) ABSTRACT

An ECG front end and a method for acquiring ECG signals are disclosed. The front end comprises a plurality of parallel measurement branches, each measurement branch comprising a protection resistor having a first terminal and a second terminal, wherein the first terminal is connectable to a respective ECG electrode. Each measurement branch comprises a first input amplifier operatively connected to the second terminal of the protection resistor and a capacitor having a first and a second terminal, wherein the first terminal of the capacitor is operatively connected to a point between the first input amplifier and the second terminal of the protection resistor and the second terminal of the capacitor is connected to a virtual ground of a second input amplifier. Each first input amplifier serves as a source of an ECG channel signal and each second input amplifier as a source of high frequency signal components.

11 Claims, 2 Drawing Sheets

ECG FRONT END AND METHOD FOR ACQUIRING ECG SIGNALS

BACKGROUND OF THE INVENTION

This disclosure relates generally to electrocardiogram (ECG) monitoring. More particularly, this disclosure relates to implementation of the front end of an ECG monitor.

As is known, the cardiac cycle can be measured non-invasively by attaching small electrodes on the skin of the patient. The voltage differences caused by the heart between the electrodes are measured and recorded to obtain the electrocardiogram (ECG) of the patient. ECG electrodes may also be used to measure a respiratory signal from the patient. For this, a high frequency excitation signal well above the ECG frequencies is normally supplied to the patient. Thus, although filters are used to reduce environmental interferences, certain frequencies higher than the actual ECG frequencies have to be passed to the monitor. In order to be able to record the weak voltages in all circumstances for all patients, the measurement is faced with many challenges. To meet the challenges, the complexity of the front end inevitably increases, if too many compromises are not to be made.

In practice, the ECG measurement electronics needs to be protected from the high voltage pulse of a defibrillator, as the defibrillator pulse may cause permanent damage to the ECG measurement apparatus. Furthermore, the protection is to be implemented so that the energy of the defibrillator pulse is not shunted by the measurement apparatus, which would lead to ineffective defibrillation. The ECG measurement apparatus, i.e. the ECG monitor, should also be capable of detecting pacemaker spikes from the measured waveform signals and filter out the noise and interference caused by other equipment used to treat the patient, such as an electrosurgery unit. An example of the contradictory requirements is that the electrosurgery unit requires the use of a filtering capacitor to filter out noise, while the presence of such a filter is not desirable in view of detection of the fast pacemaker spikes or other high frequency signals, such as the excitation signal. Unless filtered away, the high frequency noise generated by the electrosurgery unit is downconverted in a clamp circuit required to shunt defibrillator currents. The clamp circuit is normally needed, although it produces additional (low frequency) noise in presence of unfiltered high frequency noise from e.g. an electrosurgery unit.

The contradictory requirements have led to an implementation in which the protection resistors form parallel and dedicated input branches for the actual ECG signal on one hand and for the pacemaker spikes and respiratory signals on the other hand. In each input branch the protection resistor drops the defibrillator output voltage, which is of the order of 5 kV, to a level of about 5 volts or below. Considering that a well-designed ECG front end includes 2 or 3 protection resistors for each ECG electrode, the total number of protection resistors becomes rather high. This translates to high space requirement, cumbersome practical circuitry, and high cost. Furthermore, increased number of protection resistors results in increased number of parallel input branches, which tends to increase the input impedance imbalance of the front end circuitry. This, in turn, detracts from the ability of the circuitry to reject common mode noise.

BRIEF DESCRIPTION OF THE INVENTION

The above-mentioned problems are addressed herein which will be comprehended from the following specification.

In order to decrease the total number of protection resistors, no parallel protection resistors are used for the ECG and high frequency signals, but the capacitor needed as a filtering element is connected to a virtual ground of the amplifier that serves as an input amplifier for the high frequency signals. That is, the capacitor is used to divide each input lead into two branches, thereby allowing the two branches to use the same protection resistor.

In an embodiment, an ECG front end arrangement for an ECG monitor comprises a plurality of parallel measurement branches, each measurement branch comprising a protection resistor having a first terminal and a second terminal, wherein the first terminal is connectable to a respective ECG electrode. Each measurement branch comprises a first input amplifier operatively connected to the second terminal of the protection resistor and a capacitor having a first and a second terminal, wherein the first terminal of the capacitor is operatively connected to a point between the first input amplifier and the second terminal of the protection resistor and the second terminal of the capacitor is connected to a virtual ground of a second input amplifier. Each first input amplifier serves as a source of an ECG channel signal and each second input amplifier as a source of high frequency signal components.

In another embodiment, a method for acquiring ECG signals for an ECG monitor comprises forming a plurality of parallel measurement branches, each measurement branch comprising a protection resistor having a first terminal and a second terminal, wherein the first terminal is connectable to respective ECG electrode and connecting, in each measurement branch, the second terminal of the protection resistor operatively to a first input amplifier. The method further comprises connecting, in each measurement branch, a first terminal of a capacitor operatively to a point between the second terminal and the first input amplifier and a second terminal of the capacitor to a virtual ground of a second input amplifier and acquiring, in each measurement branch, an ECG channel signal from the first input amplifier and high frequency signals from the second input amplifier.

The invention is useful in all applications where minimizing bulky high voltage resistors is beneficial, and where separation of low frequency and higher frequency signals is carried out close to the input of the ECG front end circuitry.

Various other features, objects, and advantages of the invention will be made apparent to those skilled in the art from the following detailed description and accompanying drawings.

DETAILED DESCRIPTION OF THE INVENTION

Figure 1:
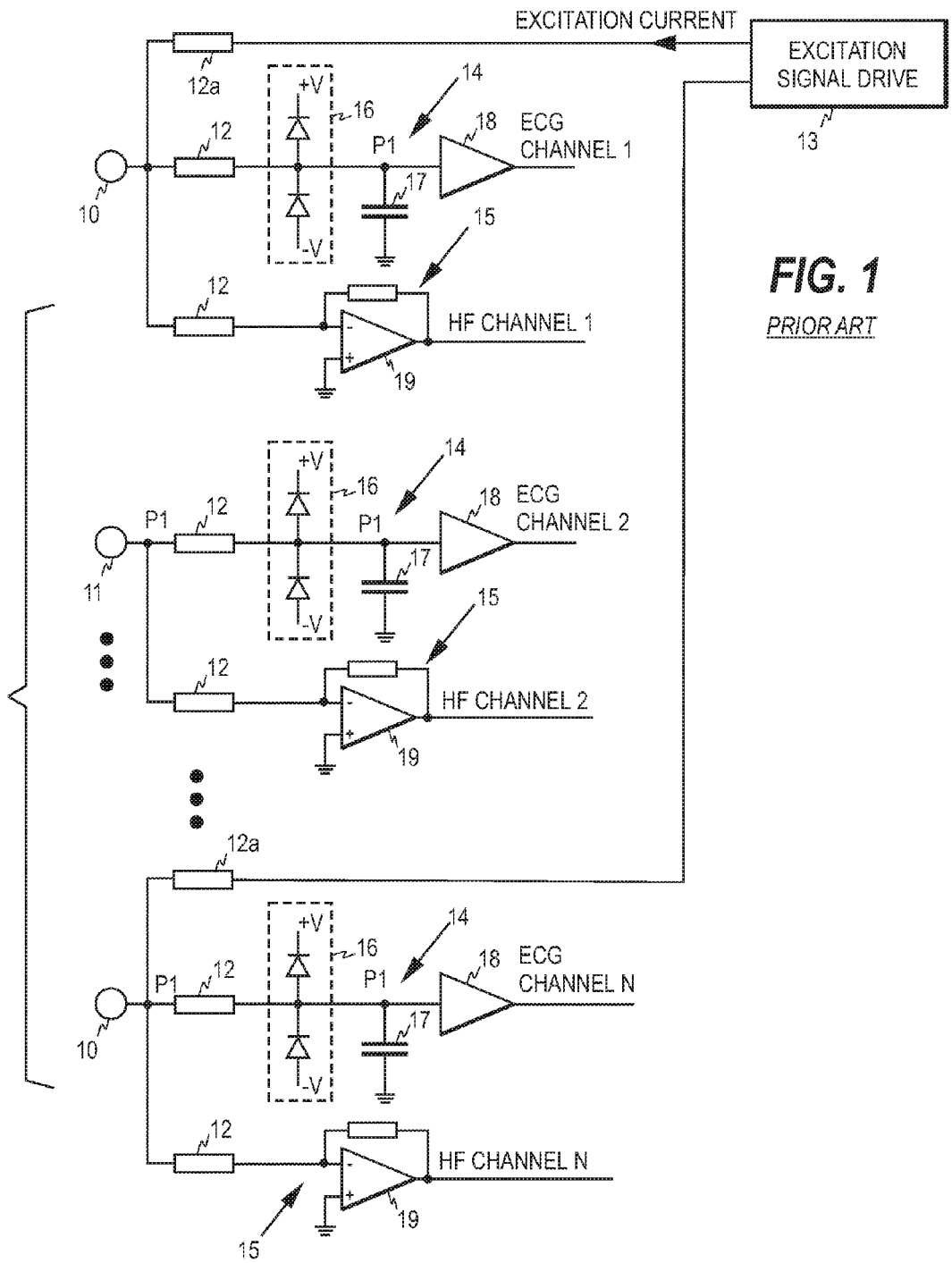
FIG. 1 illustrates a prior art ECG front end provided with ECG-derived respiration measurement.

To demonstrate the basic requirements of an ECG front end, a prior art ECG front end is discussed first. FIG. 1 illustrates an example of a typical prior art ECG front end provided with ECG-derived respiration measurement. The front end is connected to a set of N (N≥3) ECG electrodes comprising typically two outermost electrodes 10 and N−2 middle electrodes 11.

In this example, the measurement arrangement comprises 2N protection resistors 12 that protect the front end from the high voltage pulses of a defibrillator. In addition, the measurement arrangement comprises two additional protection resistors 12a needed for the respiration measurement. The total number of ECG electrodes is thus 2N+2 in this example. Each outermost electrode 10 is connected to two protection resistors 12 and to one additional protection resistor 12a, while each middle electrode 11 is connected to two protection resistors 12. Due to the ECG-derived respiration measurement, each outermost electrode 10 thus requires an additional protection resistor 12a. In the ECG-derived respiration measurement a high frequency excitation source 13 is typically connected to two electrodes, which are normally the outermost electrodes 10. A high frequency excitation current is supplied from the source to one of the outermost electrodes 10 through the respective additional protection resistor. The voltage between the two outermost electrodes is then proportional to the impedance of the signal path formed between the electrodes. The impedance measured is typically the transthoracic impedance of the patient, i.e. the outermost electrodes are normally attached to opposite sides of the thorax. From the impedance measurement, a respiratory signal may be obtained, which is indicative of the respiration rhythm of the patient. The transthoracic impedance is also useful in deriving an impedance cardiac signal (impedance cardiography, ICG) indicative of the mechanical pumping action of the heart and the flow of blood in the aorta.

Apart from the two additional protection resistors 12a of the ECG-derived respiration measurement, each ECG electrode is connected through a dedicated protection resistor 12 to a first input branch 14, termed an ECG measurement branch in this context, and through another dedicated protection resistor 12 to a second input branch 15, termed a high frequency measurement branch in this context.

Each ECG measurement branch 14 comprises a clamp circuit 16, a filtering capacitor 17, and a first input amplifier 18, which is here a non-inverting operational amplifier. Each clamp circuit comprises two diodes and each protection resistor 12 connects the respective ECG electrode to the input terminal of the first input amplifier 18. The input terminal here forms a common pole P1 for the filtering capacitor and the diodes of the clamp circuit; one (forward) diode of the clamp circuit connects the said pole to positive operating voltage +V, while the other (reverse) diode connects the said pole to negative operating voltage −V, and the filtering capacitor connects the said common pole to ground. The signal of an individual ECG channel is obtained from the output of the first input amplifier 18. That is, N ECG channels are supplied to the ECG monitor.

Each high frequency measurement branch 15 comprises a second input amplifier, which is here an inverting operational amplifier 19. The respective electrode is connected through a protection resistor 12 to the inverting input of the second input amplifier, while the non-inverting input of the amplifier is connected to ground. The high frequency signals, i.e. pacemaker peaks and the impedance signal, may be obtained from the output of the second input amplifier.

The above design of an ECG front end is a result of a plurality of requirements, which are at least partly contradictory to each other, as is discussed below.

First, the protection resistors need to be close to the ECG electrodes, thereby to drop the defibrillator voltage, which is about 5 kV, to a level of about 5 volts, so that the ECG measurement apparatus is not damaged by the high voltage pulse. The remaining current of the defibrillator pulse may still be needed to be shunted and therefore the protection resistor is coupled with a clamp circuit that shunts the current generated by the defibrillator through power supply rails. Second, the use of various electrical devices, such as an electrosurgery unit, causes electrical noise/interference, which causes low frequency noise when clipping in the clamp circuit. To filter out such noise before the first input amplifier, one or more filtering capacitors 17 are connected to ground at pole P1. The capacitor forms a low-pass filter that passes the ECG frequencies but removes the noise and thus prevents the noise from entering the first input amplifier. Third, the ECG signal may contain pacemaker spikes which are to be detected and measured. The said spikes may be of a very short duration, especially in case of an implanted pacemaker. Since high frequency signals cannot be measured efficiently from the branch provided with the filtering capacitor, a dedicated measurement branch, i.e. high frequency measurement branch 15, is normally needed to measure the high frequency signals (pacemaker spikes and the impedance (excitation) signal). Fourth, the excitation signal needs to be supplied to the electrode side of the protection resistors, and therefore a protection resistor 12a is needed for the supply line too.

Consequently, a well-designed ECG front end provided with ECG-derived respiration and pacemaker spike detection requires the elements shown in FIG. 1. The ECG front end thus includes 2 or 3 protection resistors for each ECG channel. Due to the high defibrillation voltage, the protection resistors are bulky to prevent electrical breakdown. As a high number of such resistors are to be placed close to the electrodes, the practical implementation of the ECG front end becomes bulky, cumbersome, and also costly.

Figure 2:
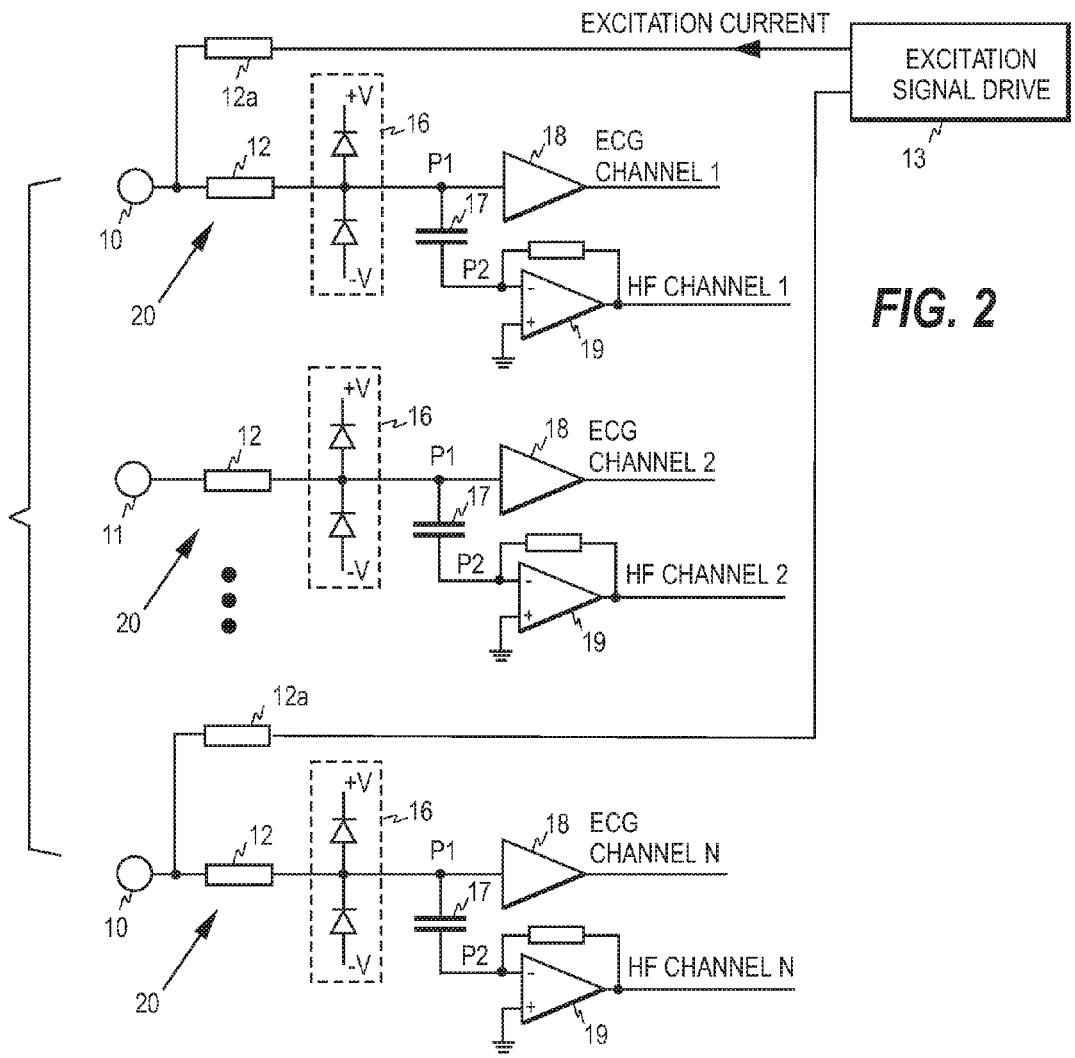
FIG. 2 illustrates an improved ECG front provided with ECG-derived respiration measurement.

To reduce the number of protection resistors, the filtering capacitor 17 is not connected to ground, but to virtual ground. That is, instead of connecting the filtering capacitor to ground, the capacitor is connected to a node that is maintained at a steady reference potential. Using the circuitry of FIG. 1 to illustrate the improvements, this node is the inverting input P2 of the second input amplifier 19, as is illustrated in FIG. 2. In this way, the protection resistor of the high frequency measurement branch of FIG. 1 may be removed from the circuitry. Apart from these changes, the ECG front end of FIG. 2 is similar to that of FIG. 1, and therefore the circuitry of FIG. 2 is described only in view of the modifications. In FIG. 2, same reference numbers are used as in FIG. 1 to designate same elements.

The embodiment of FIG. 2 thus comprises a measurement branch 20 for each ECG electrode. Each measurement branch comprises a protection resistor 12 connected to the respective ECG electrode, thereby to protect the rest of the measurement branch from the defibrillator pulse. Each measurement branch further comprises a clamp circuit 16, thereby to shunt the current generated by the defibrillator pulse through power supply rails. The first terminal of the filtering capacitor 17 is connected to the common pole P1 and the second terminal to the virtual ground of the second input amplifier 19. Consequently, each measurement branch is divided, at common pole P1, into the ECG and high frequency measurement branches by connecting the filtering capacitor to the virtual ground of the inverting amplifier 19. The high frequency signal components that are filtered out at the input of the first input amplifier 18 are present at the output of the inverting amplifier 19, and therefore pacemaker spikes and an impedance signal may be obtained from the said output.

In the embodiment of FIG. 2, the number of protection resistors is reduced to N+2. This makes the practical implementation of the ECG front end less cumbersome and significantly reduces the space requirement and cost of the ECG front end. Furthermore, by reducing the number of input branches, the front end improves the input impedance balance of the ECG measurement and thus also the rejection of common mode noise. The standards require good common mode rejection with source impedance, i.e. patient electrode, imbalance, and by reducing the number of input branches this imbalance is reduced. The division of the measurement branch 20 into two parts through the filtering capacitor maintains the advantage of being able to design the input amplifier circuit for slow signals and the inverting amplifier circuit for fast signals. This reduces both the total energy consumption and the costs. The reduction of the protection resistors is also useful in view of the ICG measurement. The ICG benefits from the ability to have a few high frequency excitation channels but multiple readout channels, and therefore the benefits of the reduction of the number of defibrillation protection resistors are apparent particularly in ICG front ends.

Figure 3:
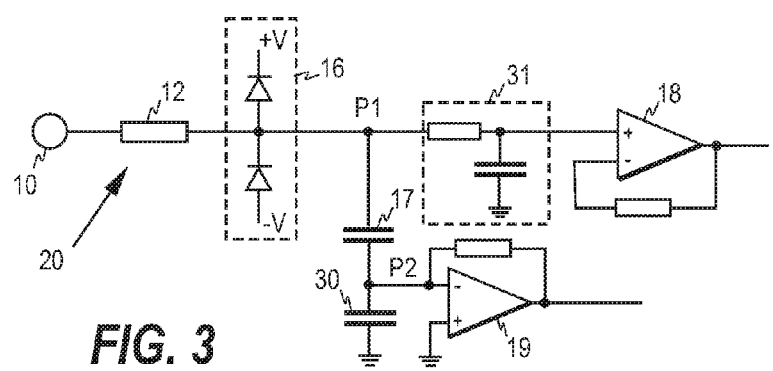
FIG. 3 illustrates a further embodiment of a single measurement branch of the ECG front end of FIG. 2.

In other embodiments of the ECG front end, various modifications may be made to the structure shown in FIG. 2. These modifications are mainly dictated by the specifications that the practical implementation is to fulfill. For example, an additional capacitor 30 may be connected from the virtual ground to ground, thereby to filter radio frequency interferences. Furthermore, an additional low-pass filter unit 31 may be added to the input of the first input amplifier. These variations are illustrated in FIG. 3, which shows only one of the parallel measurement branches 20. It is also possible to achieve the benefits of the reduction of the protection resistors by using a simpler circuitry than the one described above. For example, it is not necessary to use the clamp circuit 16, if the defibrillator pulse energy remaining after the protection resistor cannot harm the equipment. If a clamp circuit is used, a circuit comprising two diodes provides a simple and cost-effective way of implementing the clamping.

Although the virtual ground is a concept normally related to operational amplifiers, it is also possible to implement the inverting amplifier circuit by discrete transistors. Consequently, virtual ground here refers to a pole maintained at a steady reference potential.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural or operational elements that do not differ from the literal language of the claims, or if they have structural or operational elements with insubstantial differences from the literal language of the claims.

The invention claimed is:

1. A method for acquiring ECG signals for an ECG monitor, the method comprising:
    forming a plurality of parallel measurement branches, each measurement branch comprising a protection resistor having a first terminal and a second terminal, wherein the first terminal is connectable to a respective ECG electrode to receive an electrode specific signal for the measurement branch;
    connecting, in each measurement branch, the second terminal of the protection resistor operatively to a first input amplifier;
    connecting, in each measurement branch, a first terminal of a capacitor operatively to a point between the second terminal and the first input amplifier;
    connecting, in each measurement branch, a second terminal of the capacitor to a virtual ground of a second input amplifier; and
    acquiring, in each measurement branch, an ECG channel signal from the first input amplifier and high frequency signals from the second input amplifier, wherein the ECG signal and the high frequency signal are acquired from the electrode signal for the measurement branch.

2. The method according to claim 1, further comprising adapting, in each measurement branch, a clamp circuit between the first input amplifier and the second terminal of the protection resistor.

3. The method according to claim 1, further comprising connecting a high frequency excitation signal source operatively to two additional protection resistors, thereby to obtain an impedance signal from ECG electrodes connected to the two additional protection resistors.

4. The method according to claim 1, further comprising connecting an additional capacitor from the virtual ground to ground, thereby to reduce radio frequency interference.

5. An ECG front end arrangement for an ECG monitor, the arrangement comprising:
    a plurality of parallel measurement branches, each measurement branch comprising a protection resistor having a first terminal and a second terminal, wherein the first terminal is connected to a respective ECG electrode to receive an electrode specific signal for the measurement branch,
    wherein each measurement branch comprises
    a first input amplifier operatively connected to the second terminal of the protection resistor; a second input amplifier; and
    a capacitor having a first and a second terminal, wherein the first terminal of the capacitor is operatively connected to a point between the first input amplifier and the second terminal of the protection resistor and the second terminal of the capacitor is connected to a virtual ground of the second input amplifier,
    wherein each first input amplifier serves as a source of an ECG channel signal and each second input amplifier as a source of high frequency signal components, the ECG signal and the high frequency signal are acquired from the electrode signal for the measurement branch.

6. The arrangement according to claim 5, further comprising a clamp circuit adapted between the first input amplifier and the second terminal of the protection resistor.

7. The arrangement according to claim 6, wherein the clamp circuit comprises two diodes.

8. The arrangement according to claim 5, further comprising two additional protection resistors, each additional protection resistor being operatively connected to a high frequency excitation signal source.

9. The arrangement according to claim 8, wherein each of the two additional protection resistors are connected to a designated ECG electrode.

10. The arrangement according to claim 5, wherein the second input amplifier comprises an inverting operational amplifier, in which an inverting input of the inverting operational amplifier forms the virtual ground.

11. The arrangement according to claim 5, further comprising an additional capacitor connected from the virtual ground to ground, thereby to reduce radio frequency interference.

* * * * *